United States Patent [19]

Dobos-Hardy

[11] Patent Number: 5,092,886
[45] Date of Patent: Mar. 3, 1992

[54] IMPLANTABLE ARTIFICIAL KIDNEY

[76] Inventor: Matyas Dobos-Hardy, Visegradi u., 38/a, H-1132 Budapest, Hungary

[21] Appl. No.: 466,284
[22] PCT Filed: Sep. 29, 1988
[86] PCT No.: PCT/HU88/00064
§ 371 Date: Mar. 26, 1990
§ 102(e) Date: Mar. 26, 1990
[87] PCT Pub. No.: WO89/02756
PCT Pub. Date: Apr. 6, 1989

[30] Foreign Application Priority Data
Sep. 29, 1987 [GB] United Kingdom ............... 8722854

[51] Int. Cl.[5] .................................. A61F 2/04
[52] U.S. Cl. ........................................ 623/12
[58] Field of Search ............ 623/11, 12; 604/4, 5

[56] References Cited

U.S. PATENT DOCUMENTS

| | | | |
|---|---|---|---|
| 2,715,097 | 8/1955 | Guarino | 604/5 |
| 4,222,869 | 9/1980 | Kato | 604/5 |
| 4,354,933 | 10/1982 | Lester | 604/5 |
| 4,634,447 | 1/1987 | Isono et al. | 623/11 |
| 4,648,865 | 3/1987 | Aigner | 604/4 |
| 4,769,037 | 9/1988 | Midcalf | 623/12 |
| 4,770,852 | 9/1988 | Takahara et al. | 623/12 |

FOREIGN PATENT DOCUMENTS 1479002  7/1977  United Kingdom ............... 623/12

Primary Examiner—David J. Isabella
Attorney, Agent, or Firm—Herbert Dubno

[57] ABSTRACT

The invention relates to an artificial kidney having a blood inlet for connection to the renal artery of the living human organism and a blood outlet for connection fot the renal vein of the living human organism, where the blood tubes of the glomerulus of the artificial kidney that connect to the blood inlet are separated from the filtrate tubes by a permeable porous wall allowing ultra-filtration therethrough.

The artificial kidney according to the invention has an outer cover having a size and shape in accordance with that of the kidney of the living human organism, and said cover contains filtrate tubes in the tubules under the glomerulus and said tubes connect to the filtrate tubes of the glomerulus; the blood tubes of the tubules are separated from the filtrate tubes by a porous wall acting as an ultra filter; and the outlet of the filtrate tubes of the tubules is the urine outlet of the artificial kidney, whch can be connected to the ureter of the living human organism.

5 Claims, 4 Drawing Sheets

IMPLANTABLE ARTIFICIAL KIDNEY

CROSS REFERENCE TO RELATED APPLICATIONS

This application is a national phase application of PCT/HU88/00064 filed Sept. 29, 1988 based upon a U.K. national application 8722854 filed Sept. 29, 1987 under the International Convention.

FIELD OF THE INVENTION

The invention relates to an implantable artificial kidney having a blood inlet for connection to the renal artery of a living human body, a blood outlet for connection to the renal vein of the living human body and at least one glomerulus provided with blood tubes connected to the blood inlet separated from the filtrate tubes by permeable porous walls allowing ultra-filtration therethrough.

BACKGROUND OF THE INVENTION

As is known, the kidneys of the living human body are important excretory organs whose main functions are to excrete both the biologically useless materials accumulated in the blood and the superfluous water and to remove them in the form of urine. The living kidney is composed of about 1-1.5 million microscopic subunits called nephrons. Each nephron is composed of two parts: the glomerulus and the tubules. The glomerulus is built up of capillary vessels, and blood plasma is filtrated from blood through the porous wall of these vessels. Then the filtrate drains from Bowman's capsule enclosing the glomerulus to the tube system forming the tubules. The blood follows the tubules in the capillary efferent vessels starting in the Bowman's capsule and reabsorbs such an amount of water and solutes from the filtrate passing through the tubules as is necessary to restore the oncotic pressure value satisfying the Gibbs-Donnan equilibrium. The filtrate then transforms further along the tubules into urine as a consequence of this reabsorption process. It drains into the central funnel of the renal pelvis and hence into the ureter and is stored in the urinary bladder. The process carried out in the glomerulus is an ultra filtration essentially during which a great deal of water and in it dissolved solids are filtered from the blood. The blood loses approximately 50% of its aqueous content at this stage. In the tubules, the major part —approximately 80-90%—of this filtrate is reabsorbed into the efferent blood vessels together with the dissolved materials therein necessary for the blood. The remaining liquid containing also all the biologically useless materials in a high concentration is the urine that passes through the ureter to the urinary bladder. Approximately 180 liters per day of blood passes through the kidneys producing only approximately 1.5 liters of urine.

When kidneys cannot operate properly, useless materials accumulate first in the blood, then in the body and can lead to death within 10-12 days. That is why several methods have long been being experimented with for replacing a kidney unable to perform its task.

One of the methods is the implantation of a healthy kidney replacing the ill one. The disadvantage of this method is that the body rejects the foreign organ and expels it. For preventing rejection the donor is preferably a near relative. If the donor is a stranger or if a removed kidney is transplanted from a recently deceased person then anti-rejection drugs are given to the recipient patient. These drugs can not be taken ad infinitum due to their harmful side-effects; therefore a transplated kidney cannot generally be expected to keep functioning for more than five years using this method.

Another method is dialysis performed by external dialyzers. This method basically replaces the filtration process taking place in the glomerulus. On the one hand the filtrate that is generated and contains several kinds of materials necessary for blood is removed together with water and on the other hand the thickened blood is returned into the body. This method is rather expensive, unpleasant and inconvenient for the patient and can be regarded only as a temporary solution. A patient must spend three or four periods of eight to twelve hours each week connected to the dialyzer. The patient will feel unwell both before and after dialysis. Before dialysis the waste products build up in the body, and after dialysis, there is an upset of the balance of the chemical processes of the body by removal of too much of the solutes.

The other phase of the kidney's work taking place in the tubules has been regarded as biochemical process so far. Therefore no attempts have been made for returning the proper part of the water and the solutes of the filtrate.

Efforts have been made to help patients suffering from kidney malfuncion and calling for dialysis by eliminating the immobility of the patients and making the dialyzers portable and attachable to the patient's body under the clothing (see U.S. Pat. No. 3,864,259). However, not even this method is able to eliminate the above-mentioned disadvantages of dialysis and, moreover, the portability outside the body raises new problems during the contact with the environment.

The U.S. Pat. No. 4,354,933 describes a dialyzer filtering the water and the solutes out of the patient's blood in a closed unit and suggests that the closed unit be built in the patient's body. In one of the having three tubes, an arterial blood tube, a situated having three tubes: arterial blood tube, venous blood tube and a so-called urine tube between them. The urine tube is separated from the arterial blood tube and the venous blood tube by an ultra-filtering wall.

The filtrate from the arterial blood tube is led into the patient's urinary bladder and is removed from the body through it. However, this filtrate still contains valuable, metabolically important molecules missing from the patient's bloodstream. These molecules are intended to be replaced so that the blood which is led through the so-called venous blood tubes while flowing back to the patient's bloodstream is led through a bath consisting of a dialysing solution of a given composition in the other chamber of the closed unit, and from this bath the venous blood receives the valuable filtrated materials missing from the body.

The venous blood thus enriched promotes the absorbtion into the tube system from the arterial blood tube to the urine tube, according to the patent specification.

The physical-chemical feasibility of the scheme according to the U.S. Pat. No. 4,354,933 raises serious doubts. The chemical composition of the described dialyzing fluid has an oncotic pressure that enables the dialyzing fluid to extract water and other dissolved materials from the blood but does not enable it to enriching the same. Therefore it is doubtful what the venous blood could receive from the dialyzing bath.

The described process has many other additional deficiencies. The operation of the system does not seem to be resolvable without ensuring separate sucking. I.e., blood must be pumped through. Because the bulk of the patients suffering from kidney malfunction have also hypertiony, the suggested process would further increase the blood pressure.

The most considerable drawback of that closed system is that it cannot actually be separated from the surrounding environment in a sterile way because a tube leads out of the chamber containing the dialyzing fluid to the open air from the patient's body through the patient's skin. Through this tube the dialysing fluid must be changed every now and then. Such outlets represent a permanent danger of infection and threaten a life of the patient who may be also less able to combat infections.

The common feature of all the earlier approaches is that they can replace partly only the glomerular function of the kidney.

OBJECT OF THE INVENTION

The object of the present invention is to eliminate the drawbacks of the dialyzer and to provide an implantable kidney which is suitable for replacing both processes taking place in the kidney, is simple and eliminates the immobility of the patients connected to the machine.

SUMMARY OF THE INVENTION

The artificial kidney of the invention has a blood inlet for connection to the renal artery of the living human organism and a blood outlet for connection to the renal vein of the living human organism, the blood tubes of the glomerulus of the artificial kidney that connect to the blood inlet being separated from the filtrate tubes by a permeable porous wall allowing ultra-filtration therethrough. According to the invention the artificial kidney has an outer cover having a size and shape in accordance with that of the kidney of the living human organism, and the cover contains filtrate tubes in the tubules under the glomerulus. These tubes connect to the filtrate tubes of the glomerulus. The blood tubes of the tubules are separated from the filtrate tubes by a porous wall acting as an ultra filter. The outlet of the filtrate tubes of the tubules is the urine outlet of the artificial kidney, which can be connected to the ureter of the living human organism.

The blood tubes and filtrate tubes of the artificial kidney can form a tube system consisting of tubes embedded in one another so that the inner tubes are separated from the surrounding outer tubes by permeable porous walls allowing ultra-filtration, and the outer tubes can have impermeable walls.

The blood tubes in the glomerulus of the artificial kidney can be formed by the inner tubes and the filtrate tubes can be formed by the outer tubes surrounding the inner tubes. Cross-over points are formed between the glomerulus and the tubules so that the inner tubes of the tubules form the filtrate tubes and the outer tubes surrounding the inner tubes form the blood tubes.

The outer cover advantageously is made of flexible, impermeable, bio-compatible plastic materials such as polytetrafluorethylene, polyurethane or silicone rubber. The permeable porous walls that allow the ultra-filtration can be made of polyurethane.

The outer cover is advantageously surrounded by a lobe that enables the stitching of the artificial kidney into the living human organism.

In the blood inlet of the artificial kidney that serves for connecting to the renal artery, a control valve is provided to act as a back-pressure valve suitable to maximize the blood pressure.

The invention is based upon a scientific realization that the resorption of the filtrate in the tubules toward the blood, in the vessels leading beside the tubules is performed not during a biochemical process but by a biophysical process from the tubules of the living kidney; therefore the blood plasma filtered from the glomerulus of the same nephron, together with the complex molecules, e.g. glucoses, ureas, potassium, sodium etc. filtered too from the glomerulus, goes back to the blood by a biophysical way from the filtrate in the tubules with the help of the osmotic pressure, while the biologically useless chemicals in the filtrate cannot be reabsorbed into the blood.

It has been found that the biophysical processes described above taking place in the kidney of the living human body can be modelled by means of bio-compatible plastic having a preferable filtering feature with a geometrical size corresponding to that of the living kidney, so there are no obstacles to the human implantation of the artificial kidney of the invention.

According to the present invention the artificial kidney has an outer cover having a size and shape in accordance with that of the kidney of the living human body, and the cover contains filtrate tubes in the tubules under the glomerulus and the tubes are connected to the filtrate tubes of the tubules. The blood tubes of the tubules are separated from filtrate tubes by a porous wall which acts as an ultra filter and the outlet of the filtrate tubes of the tubules is the urine outlet of the artificial kidney connected to the ureter of the living human body.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
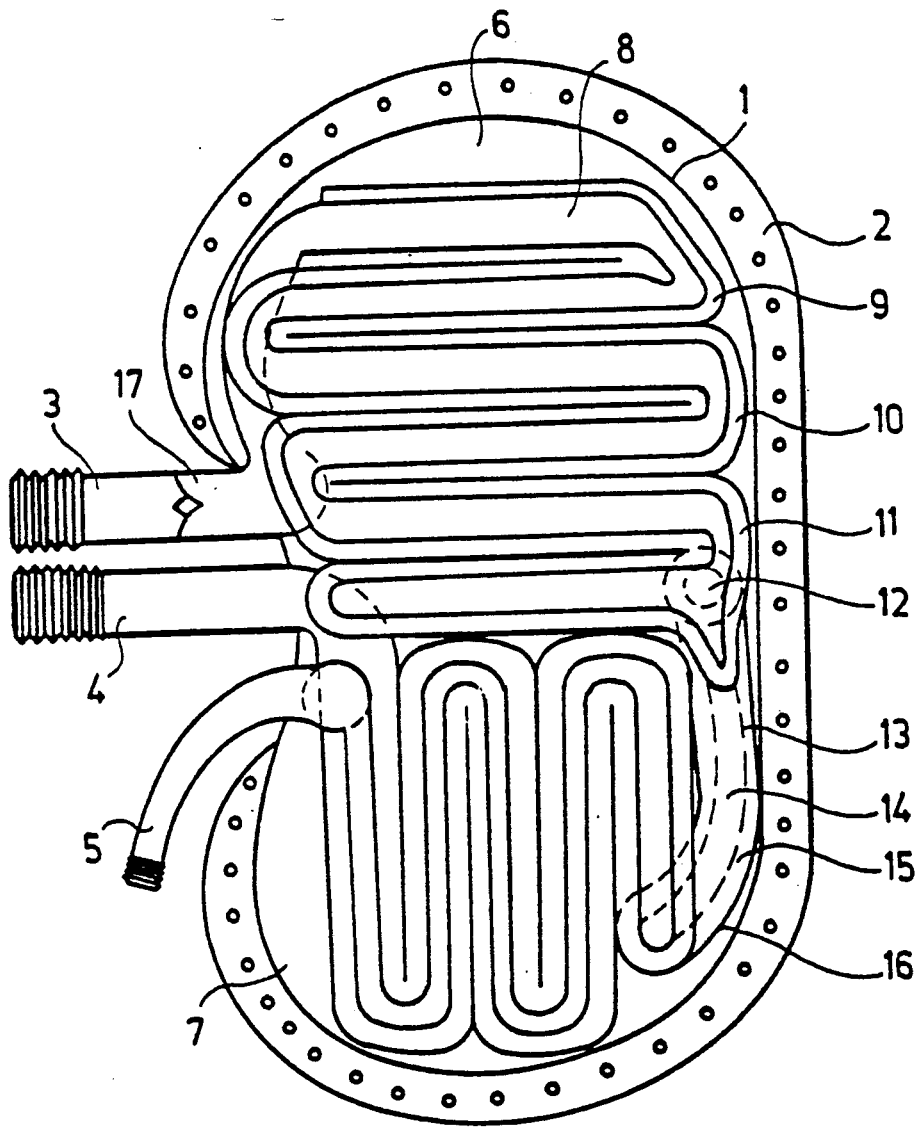
FIG. 1 is a sectional view of an artificial kidney according to the invention.

The artificial kidney according to FIG. 1 is provided with a cover 1 having a size and shape in accordance of those of the natural kidney of the living body; its material is a flexible, impermeable, bio-compatible plastic, e.g. polytetrafluorethylene, polyurethane or silicone rubber. The outer surface of the cover 1 is surrounded by a lobe 2 by means of which the artificial kidney can be fixed in the body. The artificial kidney has a blood inlet 3 for connection to the renal artery of the living human body, a blood outlet 4 for connection to the renal vein of the human body, and a urine outlet 5 for connection to the ureter of the living human body.

Since a human body has two kidneys, there is need for implanting two so-called macro-nephrons. The two macro-nephrons are situated in a single common cover 1 and their blood inlets 3, blood outlets 4 and urine outlets 5 are also common, respectively.

Both macro-nephrons have the following construction: While the living kidney consists of 1-1.5 million nephrons—as has been mentioned above—, the artificial kidney according to the invention consists of two (or occasionally more parallel operated) macro-nephrons that practically model the micro-nephrons of the living body's kidney, in macro dimensions. The macro-nephron consists of two main parts: the glomerulus 6 of the macro-nephron and the tubule 7 located below the glomerulus 6.

In the glomerulus 6 there are a blood tube 8 connected to the blood inlet 3 and a filtrate tube 9 surrounding the blood tube 8 and having a closed end in the region of the blood inlet 3. The blood tube 8 and the filtrate tube 9 can form a single tube system embedded into one another, where the inner tube is the blood tube 8 and the tube surrounding it and having a ring-shaped cross-section is the filtrate tube 9. However, the tube system can be formed of several parallel connected blood tubes 8 and filtrate tubes 9. The separating wall between the inner blood tube 8 and the outer filtrate tube 9 is an ultra-filtering permeable porous wall 10 whose material is e.g. polyurethane, while the outer wall of the outer filtrate tube 9 is an impermeable wall 11. The impermeable wall 11 prevents the system consisting of the blood tube 8 and the filtrate tube 9 from allowing anything out of the system. Therefore the filtrate tube 9 has to surround perfectly the blood tube 8 provided with the porous wall 10.

Figure 2:
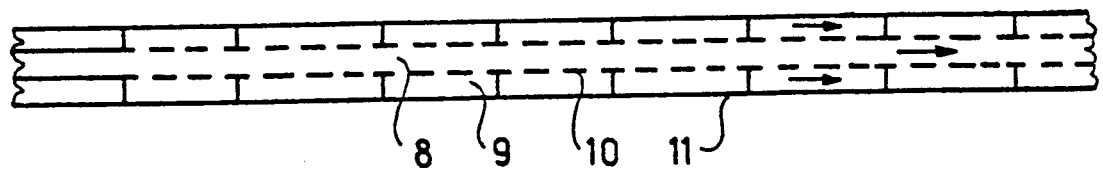
FIG. 2 is the sectional view of the inner and outer tubing of the glomerulus of the kidney of FIG. 1.

The tube system consisting of the inner and outer tubes is shown in FIG. 2 in detail. Here the porous wall 10 between the blood tube 8 and the filtrate tube 9 and the impermeable wall 11 surrounding the outer tube can be seen.

The tubule 7 is built up similarly to the glomerulus 6. The only difference is that a cross-over point 12 is formed between the glomerulus 6 and the tubule 7 where the blood tube 8 forming the inner tube in the glomerulus 6 connects to the blood tube 13 forming the outer tube of the tubules 7 and the filtrate tube 9 forming the outer tube in the glomerulus 6 connects to the filtrate tube 14 forming the inner tube of the tubule 7. The separating wall between the filtrate tube 14 and the blood tube 13 is also an ultra-filtering porous wall 15, while the outer wall of the blood tube 13 is an impermeable wall 16. In this case the tube system can be constructed from several parallel connected blood tubes 13 and filtrate tubes 14. The filtrate tube 14 connects to the urine outlet 5, while the blood tube 13 connects to the blood outlet 4.

Figure 3:
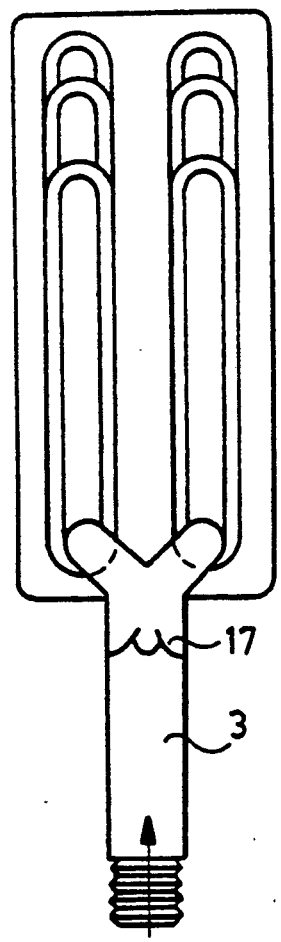
FIG. 3 shows the junction for two macro-nephrons of the artificial kidney at the blood inlet connectable to the renal artery similar to the renal vein connection.

FIG. 3 shows the junction of the blood inlet 3 for two macro-nephrons of an artificial kidney. In the blood inlet 3 a control valve 17 is arranged preferably upstream of the junction. The control valve 17 is formed as a nonreturn valve which does not allow the increase of the blood pressure above 75 mm of mercury.

Figure 4:
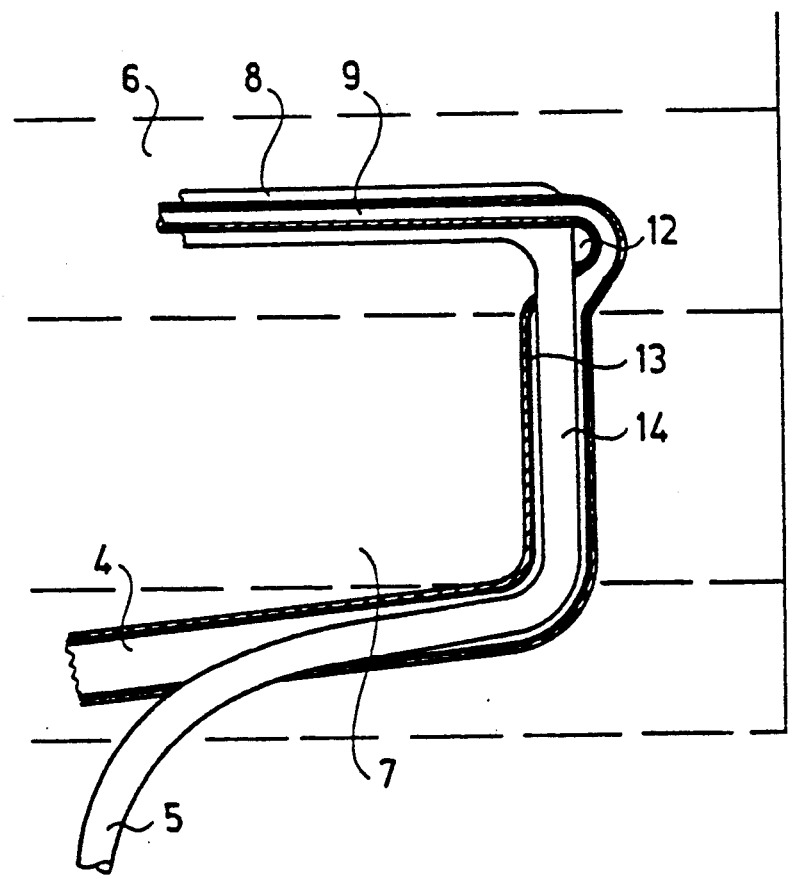
FIG. 4 is a partial diagrammatic view of the crossover between the glomerulus and tubules of the artificial kidney.

FIG. 4 shows a possible cross-over point 12. Care should be taken at the cross-over point 12 in order to prevent the impermeable walls 11, 16 from allowing anything to flow out of the tube system.

Figure 5:
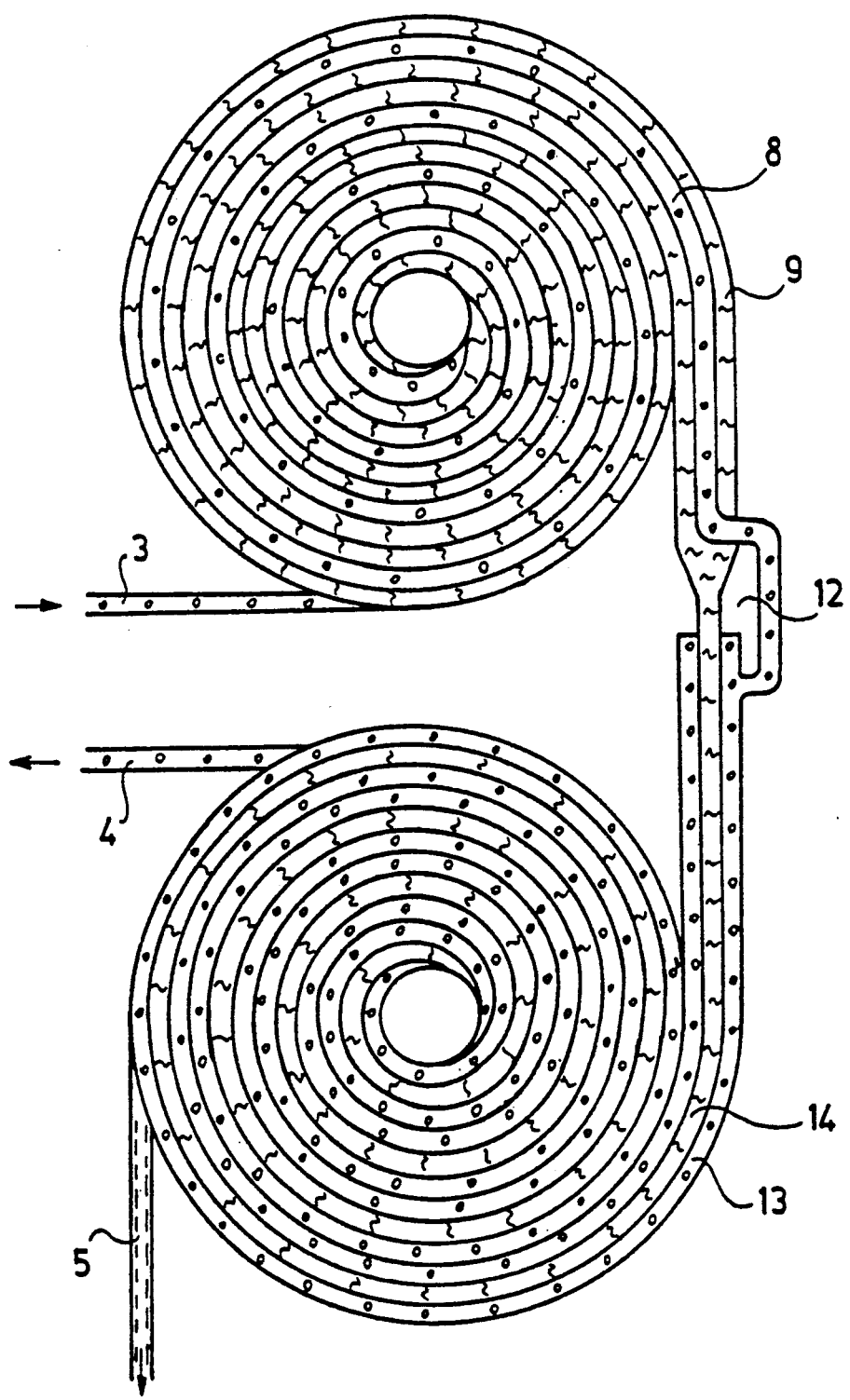
FIG. 5 shows another embodiment of the invention where the inner and outer tubes are located spirally in the glomerulus and tubules.

In the artificial kidney the tube systems must be situated so that the tube system of necessary length should be placed in the artificial kidney of given size and shape with the smallest break possible, i.e. without decreasing the cross-sectional area of the tubes. Of course the solution shown in FIG. 1 is only one of several different possibilities. Another construction example is shown in FIG. 5, where the tube system is situated spirally in the artificial kidney. Although it results in a certain dead space both in the glomerulus 6 and in the tubules 7 in the middle, the spiral system is preferable because of the smaller number of breaks. FIG. 5 is only a symbolic scheme, the spirals lie on each other on several layers; therefore it is possible that a certain spiral has its inlet and outlet at its greatest diameter.

The artificial kidney according to the invention operates as follows:

After implanting the artificial kidney, the blood inlet 3 is connected to the renal artery of the living body, the blood outlet 4 is connected to the renal vein of the living body, while the urine outlet 5 is connected to the ureter of the living body. In consequence of the pumping work of the heart the blood enters the artificial kidney with a blood pressure of about 90 mm of mercury while coming from the renal artery, and the control valve 17 reduces this pressure to about 75 mm of mercury. Then the blood passes through the inner blood tube 8 and during its path the cross-over point 12 the major part of the aqueous content of the blood—approximately 50%—is filtered into the outer filtrate tube 9 through the porous wall 10. Together with the water the dissolved materials also leave the inner blood tube 8 in great quantity. After the cross-over point 12, in the tubules 7 the thick blood flowing in the blood tube 13 surrounding the filtrate tube 14 reabsorbs the major part of the water and the materials valuable for the blood and for the body, in consequence of the oncotic pressure from the filtrate tube 14 through the porous wall 15, while the biologically useless materials stay in the filtrate. Therefore the filtrate passing through the tubule 7 transforms into urine and through the urine outlet 5 it enters the ureter of the body.

The artificial kidney according to the invention does not require maintenance after implantation as it does not need external power supply, the blood being driven through it by the heart. It is made of durable materials, moreover. Contrary to the implantation of a living kidney, the danger of rejection is not expected from experience. Therefore the artificial kidney according to the invention can restore the health of the patient suffering from fatal kidney malfunction for the whole of his natural life contrary to the blood dialysis as applied presently.

I claim:

1. An implantable artificial kidney, comprising:
   an outer cover having a shape of a natural kidney and formed with a lobe for affixing the artificial kidney in a living human body;
   a blood inlet leading into said cover and connectable to a renal artery of the living human body;
   a blood outlet leading from said cover and connecting to a renal vein of the living human body;
   a urine outlet leading from said cover and connectable to a ureter of the living human body;
   a glomerulus in said cover formed with a plurality of convolutions of an inner blood tube surrounded by an outer filtrate tube and separated therefrom over a collective length of said inner blood tube and said outer filtrate tube by a permeable wall of said inner blood tube forming an ultrafilter permitting filtration of an aqueous component of blood traversing said inner blood tube and dissolved substances in said aqueous component, said inner blood tube being connected at one end to said blood inlet and having an opposite end; and a tubule system below said glomerulus in said cover and having a plurality of convolutions of an inner filtrate tube connected at a cross-over point to said outer filtrate tube and an outer blood tube surrounding said inner filtrate tube and connected at said cross-over point to said opposite end of said inner blood tube, said outer blood tube and said inner filtrate tube being separated by a porous wall permitting oncotic pressure to effect passage of a major portion of water from said inner filtrate tube into said outer blood tube, said outer blood tube being connected to said blood outlet and said inner filtrate tube being connected to said urine outlet, said outer tubes having impermeable outer walls.

2. The implantable artificial kidney defined in claim 1, further comprising a control valve in said inlet forming a back-pressure valve maximizing blood pressure in said inlet.

3. The implantable artificial kidney defined in claim 1 fabricated at least in part of silicone rubber.

4. The implantable artificial kidney defined in claim 1 wherein said cover is composed of polytetrafluoroethylene.

5. The implantable artificial kidney defined in claim 1 wherein said permeable and porous walls are composed of polyurethane.

* * * * *